United States Patent [19]
Grundei et al.

[11] Patent Number: 5,634,878
[45] Date of Patent: Jun. 3, 1997

[54] IMPLANTABLE DEVICE FOR SELECTIVELY OPENING AND CLOSING A TUBULAR ORGAN OF THE BODY

[75] Inventors: Hans Grundei, Luebeck; Olaf Ahlers, Hamburg, both of Germany

[73] Assignee: ESKA Medical GmbH & Co., Germany

[21] Appl. No.: 308,582

[22] Filed: Sep. 19, 1994

[30] Foreign Application Priority Data

Sep. 17, 1993 [DE] Germany .................. 4 331 658

[51] Int. Cl.$^6$ .................................... A61F 2/02
[52] U.S. Cl. ...................... 600/30; 128/DIG. 25
[58] Field of Search ............... 600/29–32; 128/DIG. 25

[56] References Cited

U.S. PATENT DOCUMENTS

| | | | |
|---|---|---|---|
| 3,797,478 | 3/1974 | Walsh et al. | 600/29 |
| 4,222,377 | 9/1980 | Burton | 600/31 |
| 5,088,980 | 2/1992 | Leighton | 600/30 |

FOREIGN PATENT DOCUMENTS 2251302   6/1975   France .................. 128/DIG. 25

*Primary Examiner*—Angela D. Sykes
*Assistant Examiner*—John P. Lacyk
*Attorney, Agent, or Firm*—Gifford, Krass, Groh, Sprinkle, Patmore, Anderson & Citkowski, P.C.

[57] ABSTRACT

An implantable device for selectively opening and closing a tubular organ of the body such as the urethra has an elongate valve body which can be introduced into the tubular organ. The valve body has a shut-off means which can be selectively closed and opened, for which purpose the valve body has an elastic hose portion in which there is disposed an inflation body which can be inflated by a fluid to then close the lumen of the hose portion. The fluid can be conveyed out of the inflation body into a storage container by actuation of an implantable pump so the inflation body collapses and permits a flow through the valve body. Manual actuation of a non-return valve in the pump causes fluid to flow out of the storage container into the inflation body to inflate same and close the valve body.

8 Claims, 2 Drawing Sheets

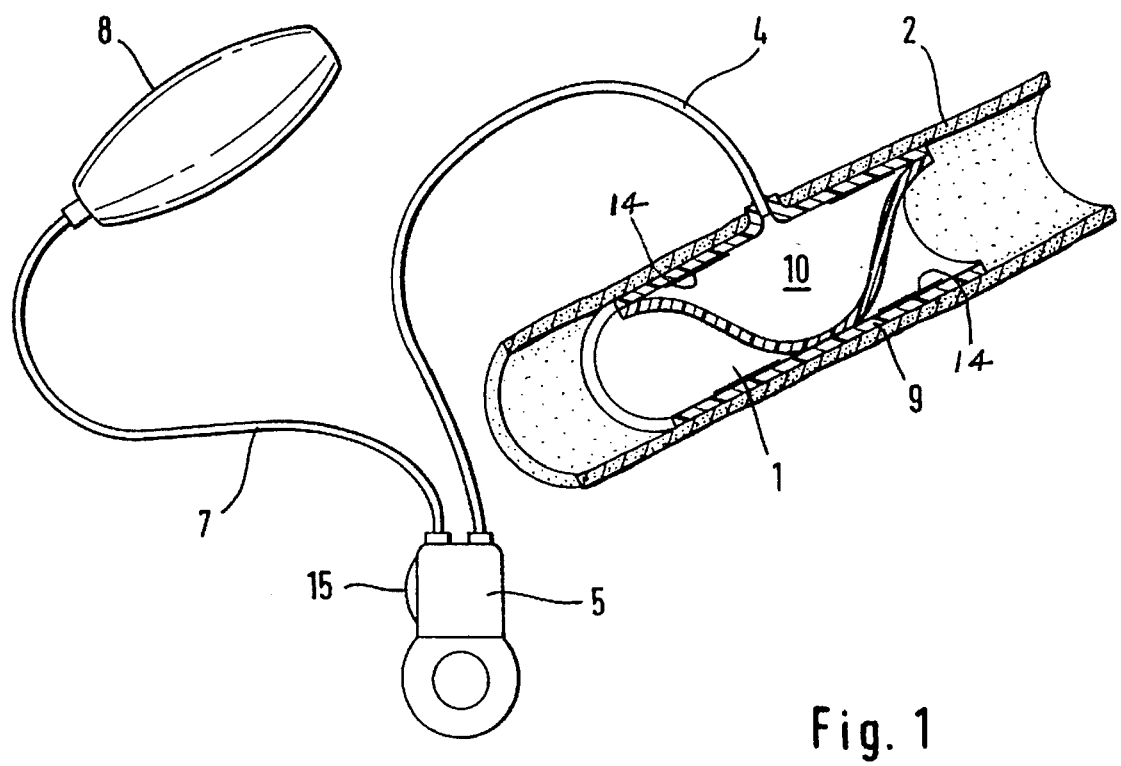
Fig. 1
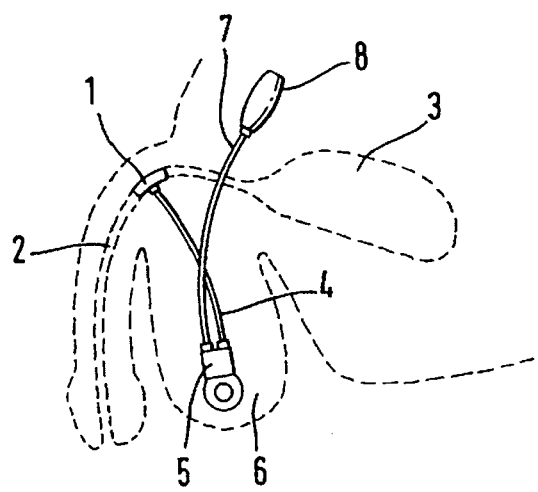

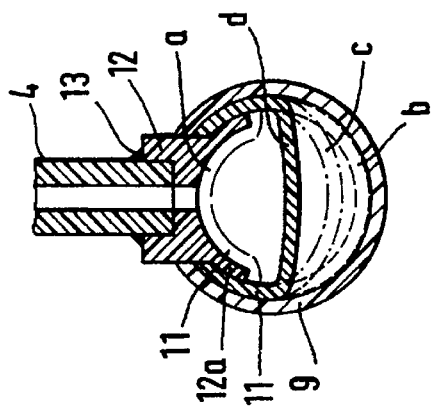
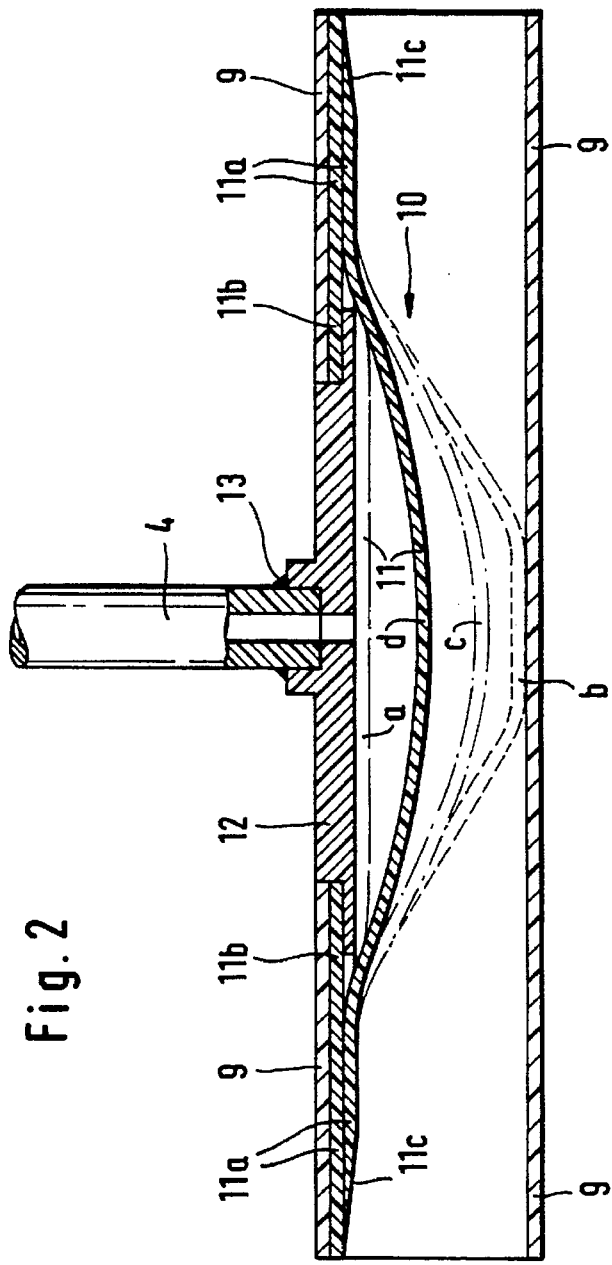
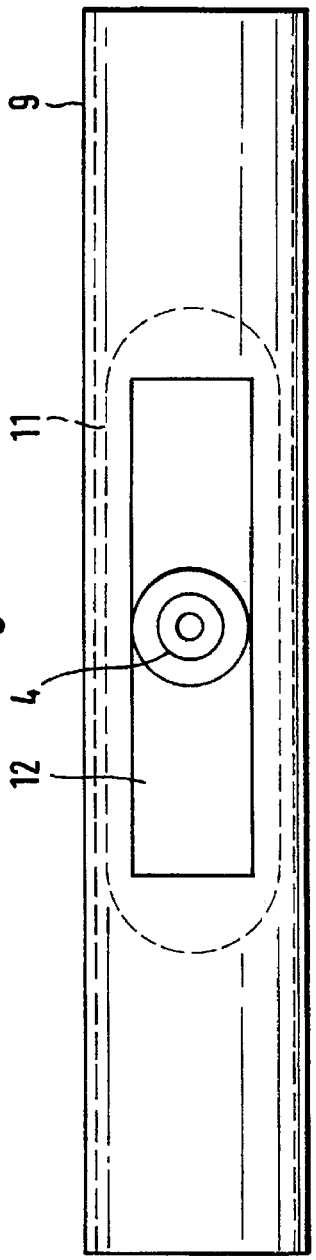

IMPLANTABLE DEVICE FOR SELECTIVELY OPENING AND CLOSING A TUBULAR ORGAN OF THE BODY

BACKGROUND OF THE INVENTION

Implantable devices for opening and closing tubular organs of the body such as in particular but not exclusively the urethra are used more particularly in the form of prostheses for the treatment of urinary incontinence, also being known as artificial sphincters. Such an arrangement uses closure means which act mechanically on the urethra and which perform the function of the natural sphincter muscle in the event of failure of the latter. Many different forms of such closure arrangements are known. For example Swiss patent specification No 463 015 discloses an implantable device for selectively opening and closing the urethra, which has clamping members that are movable towards each other to close off the urethra. The clamping members are subjected to the action of a spring and a magnet so that they can be actuated from the outside. A prosthesis is also known for male urinary incontinence (DE-GU 79 29 052), in which a cuff that surrounds the urethra permits it to be shut off by the application of a pressure thereto. The prosthesis disclosed in EP 144 699 B1 also includes a cuff which surrounds the urethra on the outside thereof, the opening or closed position of the prosthesis being produced by mechanical pressure from the outside or by liquid pressure. For that purpose the arrangement has an implanted pump with an implanted liquid reservoir.

In the above-indicated arrangements the urethra is selectively closed or opened by pressure from the exterior. However, even when very soft cuffs which act on the urethra with extreme gentleness are used as the means for closing off the urethra, necrotic damage to the urethra or the surrounding tissue with a good blood supply occurs after a comparatively short period of time, in the region of the closure member or cuff. The closure member then has to be removed to avoid aggravating the damage. It will be seen therefore that such an arrangement cannot provide a permanent solution to the problem of incontinence or even only a temporary solution for at least a relatively long period of time. A similar consideration also applies to the situation where other organs of the body are to be selectively opened or closed, for example blood vessels.

An incontinence valve is to be found in German patent specification No 41 35 502, which is formed by an elongate valve body with longitudinal bore therein, which valve body is to be introduced over its entire length into the urethra. The valve body has an open end and a closable end with a valve head. The urine is guided along the outside of the valve to at least one radially arranged communicating opening leading into the longitudinal bore, while the communicating opening can be selectively opened or closed by way of a shut-off device which is actuable from the distal end. Although that valve arrangement avoids the disadvantages of the above-discussed valves in which the urethra is compressed by a pressing force applied thereto from the outside thereof, further problems are still encountered. In particular it is not possible to insert a catheter through the valve body, as may be necessary in emergency situations and for investigation.

SUMMARY OF THE INVENTION

An object of the present invention is to provide an implantable device for selectively opening and closing a tubular organ of the body, such as the urethra, which not only permits reliable opening and closing of the organ of the body but which can further permit a catheter to be inserted or passed through the device.

Another object of the present invention is to provide an implantable device for selectively opening and closing a tubular organ of the body, which is capable of elastically following movement of the organ.

A still further object of the present invention is to provide an implantable device for selectively opening and closing a tubular organ of the body such as the urethra which is simple and reliable to operate and which affords a secure closure effect in the closed position.

In accordance with the invention the foregoing and other objects are achieved by an implantable device for selectively opening and closing a tubular organ of the body, such as the urethra, comprising an elongate valve body adapted to be introduced into the organ of the body and operable to selectively open and close said organ. The valve body includes a hose or tube portion and an inflation body disposed in the hose or tube portion and adapted to be inflated by a fluid to close the lumen of the hose or tube portion.

The inflation body is desirably formed by a balloon with which a hose or tube means communicates for a feed of fluid thereto. In general, it is desirable for the fluid to be a liquid, for example physiological common salt solution, because liquids are practically non-compressible. It is however also possible to use a gas.

In a preferred feature of the invention the balloon is formed by an inner hose portion which is closed at both ends and the outside surface of which is connected over its length and on a part of its periphery to the inside surface of the hose or tube portion, for example by adhesive or welding. The inner hose portion can advantageously be closed off by pressing flat and glueing the ends thereof, in which case the inner hose portion is connected with one side of the flattened ends and the interposed part of the periphery to the inside surface of the hose or tube portion of the valve body. In a preferred feature of that arrangement the flattened ends terminate in a generally wedge-like configuration so that they blend substantially without a step into the wall of the hose or tube portion. A catheter can then be passed through that arrangement without encountering an obstacle that might resist easy movement thereof.

Preferably the valve body comprises an elastic plastic material, more preferably silicone rubber. It is advantageously provided with a support means to restrict an increase in the diameter of the hose or tube portion, the support means being a fabric which is applied to the outside thereof or being a fabric inlay. That ensures that the urethra or the other organ of the body which is to be controlled by the device according to the invention cannot be excessively severely stretched, even if the internal pressure in the inflation body increases to a considerable level.

Preferably the fluid in the form of a liquid can be conveyed into the inflation body by way of a hose, by means of an implantable, manually operable pump means. A storage means or vessel which is also implantable is preferably connected to the pump means and the pump means has a non-return valve which is disposed in a feed line to the storage means and which is manually actuable from the exterior in such a way that, upon actuation of the pump means, liquid is sucked out of the inflation body and conveyed into the storage means to collapse the inflation body. That collapse thus opens the passage through the tube or hose portion of the valve body to permit a flow therethrough. Upon actuation of the non-return valve liquid flows under the influence of the pressure in the storage means into the inflation body and shuts off the through flow in the hose or tube portion.

Preferably the amount of liquid in the system comprising the storage means, the inflation body, the pump means and the communicating hoses is such that a given system pressure which is adequate for securely and reliably shutting off a through-flow through the valve body is not exceeded. That on the one hand prevents unnecessarily high pressures from occurring in the system, while on the other hand it provides an emergency valve function. More specifically, if for example the pressure in the bladder rises above a normal value, the inflation body of the valve device according to the invention no longer completely shuts off the through-flow through the valve body so that the rise in pressure is limited and in an emergency situation a discharge flow can take place.

Further objects, features and advantages of the invention will be apparent from the following description of a preferred embodiment.

BRIEF DESCRIPTION OF THE DRAWINGS

FIG. 1 is a diagrammatic view of an implanted device according to the invention in the form of an incontinence valve having a pump means and a storage container, implanted in a man, FIG. 2 is a view in longitudinal section through the valve body of the device shown in FIG. 1, FIG. 3 is a plan view of the valve body shown in FIG. 2, and FIG. 4 is a view in cross-section through the valve body shown in FIGS. 2 and 3.

DESCRIPTION OF THE PREFERRED EMBODIMENT

Referring to FIG. 1, the lower part thereof diagrammatically illustrates the way in which a device according to the invention is implanted in a human body, more specifically in the example illustrated, in a man.

As can be seen therefore from FIG. 1 the device comprises a valve body 1 which is fitted into a urethra 2 in a region thereof near the urinary bladder 3. In the implantation operation the urethra 2 is opened as by slitting at the appropriately selected location so that the valve body 1 can be inserted. A hose 4 leads to the valve body 1 from a pump means 5 which is inserted into the scrotum 6 in such a way that it can be felt and thus actuated, from outside. A storage means in the form of a container or vessel 8 is also connected to the pump means 5 by way of a further hose 7, and lies at a suitable location behind the abdominal wall.

As is shown on an enlarged scale in the upper part of FIG. 1, the valve body 1 which is disposed in the urethra 2 has a hose or tube portion 9, referred to herein for the sake of simplicity as a hose portion 9. The hose portion 9 accommodates an inflation body 10 which is inflated in the condition illustrated in FIG. 1 and thus closes off the hose portion 9 and therewith the urethra 2. The inflation body 10 is inflatable by means of a fluid such as more particularly a liquid such as a salt solution, which is conveyed into the inflation body 10 by way of the hose 4 by actuation of the pump means 5. The mode of operation of the plop means 5, actuation of the valve body 1 and the presure conditions in the system generally will be described in greater detail hereinafter. At this point however the valve body 1 will first be described in greater detail with reference to FIGS. 2 through 4.

The valve body 1, the parts of which are made from an elastic plastic material such as preferably silicone rubber and are connected together as by adhesive has a hose portion 9 whose length and diameter are to be matched to the respective purpose of use involved. When the device according to the invention is used as an incontinence valve and is implanted in a urethra, the outside diameter can be in the range of between 6 and 10 mm and the length can be in the range of between 20 and 80 mm, preferably being about 50 mm, depending on the anatomical conditions of each situation involved. The wall thickness is for example about 0.5 mm.

Disposed in the interior of the hose portion 9 is the inflation body which is generally identified by reference numeral 10 and which is formed from an inner hose portion 11. The inner hose portion 11 is closed at its two ends 11a shown in FIG. 2, by the ends being pressed together and thus flattened and glued. In addition the inner hose portion 11 is connected, for example by glueing, in its peripheral part 11b which is upward in the Figure and with the upper part of the inner hose portion ends 11a, to the upper part of the hose portion 9. A flattened or bevel configuration 11c at both ends 11a of the inner hose portion 11 affords a wedge-like termination for the flattened ends 11a so that they blend substantially without a step into the wall of the hose portion 9.

A flange connecting portion 12 is disposed approximately in the middle region of the interconnected parts of the inner hose portion 11 and the hose portion 9, as can be clearly seen from FIG. 4. The flange connecting portion 12 extends outwardly out of the interior of the inflation body 10 through suitable openings in the two walls of the inner hose portion 11 and the hose portion 9, and serves for connection of the hose 4 shown in FIG. 1. To provide secure sealing integrity, the hose 4 is appropriately fixed to the flange connecting portion 12 as by welding or glueing, as diagrammatically indicated at 13 in FIGS. 2 and 4. The secure and sealing connection of the flange connecting portion 12 is further assisted and enhanced by projection portions 12a which engage behind the walls of the hose portions 9 and 11 and are there also fixed in position by glueing.

FIGS. 2 and 4 show a number of positions that the non-glued part of the wall of the inner hose portion 11 can adopt. In position a the wall of the inner hose portion 11 bears against the flange connecting portion 12. The inner hose portion 11 is therefore overall collapsed, more specifically by virtue of the fact that all the liquid has been sucked out of the inner hose portion 11 by the pump means 5 by way of the hose 4 and accordingly a reduced pressure, relative to the surrounding area, has been generated. In that position the hose portion 9 of the valve body 1 can accept a flow therethrough practically without impediment, so that a discharge flow of urine or, when the device is used in relation to an organ of the body other than the urethra, a discharge flow of another body fluid, is accordingly possible. The hose portion 9 is also free for a catheter or an endoscope to be pushed therethrough.

The position of the wall of the inner hose portion 11, which is shown in broken lines and identified at b, on the other hand represents the fully closed position of the valve body 1. In that position the wall of the inner hose portion 11 bears sealingly against the inside surface of the hose portion 9. That position is attained by liquid being introduced into the inner hose portion 11 by way of the hose 4, under sufficient pressure.

A position as indicated at c in FIGS. 2 and 4 represents a neutral position, being a position in which the wall of the inner hose portion 11 is not influenced by a liquid pressure and is therefore not urged either towards the closed position b or towards the open position a. That neutral position c can be preselected by structural considerations and accordingly can also be disposed differently. The position d represents an intermediate position between positions a and c.

The system consisting of the inner hose portion 11, the pump means 5, the storage container 8 and the communicating hoses 4 and 7 is completely sealed off relative to the exterior and is filled in a bubble-free fashion with a suitable liquid, for example physiological common salt solution. For that purpose for example plug-in connections (not shown) can be provided on one or both hoses 4, 7. The internal pressure in the liquid system, which is produced when a given amount of liquid is introduced into the system, by virtue of the elastic walls of all the parts and in particular also the storage container 8, is so selected that the inner hose portion 11 adopts the closed position b when the pressure in the system takes effect.

After implantation of all parts of the device, an unimpeded discharge flow of urine can initially be ensured by means of an inserted catheter until the subject patient has healed and recovered from the surgical implantation operation. The patient can then subsequently open and close the valve arrangement as is required.

For opening the valve arrangement the pump means 5 is actuated through the skin by means of two fingers. A non-return valve (not shown) in the feed to the hose 7 ensures that liquid which is taken from the inner hose portion 11 by way of the hose 4 is pumped into the storage container 8. The wall of the inner hose portion 11 finally moves into the opened position a when all the liquid has been sucked out of the inner hose portion 11, and therefore the inflation body 10, and conveyed into the storage container 8. When the patient wants to close the valve body again, after the urine drainage operation, he presses on a lateral bulge portion 15 of the pump means 5. As a result the inner non-return valve is opened so that the liquid which is under elevated pressure in the storage container 8 flows into the inner hose portion 11 by way of the hose 4 and the inner hose portion 11 adopts the fully closed position b.

So that the pressure in the inner hose portion 11, even at elevated values, does not result in unacceptable expansion of the hose portion 9 and therewith the urethra 2, the valve body includes a support means to restrict an increase in diameter of the hose portion 9. The support means may be made of fabric and more specifically may be in the form of a fabric inlay, or a non-stretch or tension-resistant fabric or mesh (not shown) may be disposed on the outside of the hose portion 9.

It will be appreciated that the above-described device according to the invention has been set forth by way of illustration and example of the principles of the present invention and that various modifications and alterations may be made therein without thereby departing from the spirit and scope of the invention.

What is claimed is:

1. An implantable device for selectively opening and closing a lumen of a tubular organ of a body, the lumen being bounded by an inner wall of the organ, said implantable device comprising:

an elongate valve body adapted to be introduced into the organ, said valve body including a substantially cylindrically shaped hose portion lining the inner wall of the organ and an inflatable body portion sealingly secured around its periphery to an upper pan of said hose portion, a pump means communicating with said elongate valve body by a first hose, a fluid storage vessel communicating with said pump means by a second hose, a source of fluid selectively transportable between said storage vessel and said valve body upon actuation of said pump means, said fluid being transportable in a first direction to expand outwardly said inflatable body portion to close a lumen of said hose portion, said fluid being transportable in a second direction to retract said inflatable body to open the lumen, said inflatable body being formed as an elongate balloon by an inner hose having first and second ends adapted to be closed, said inner hose having an outside surface connected over its length and on a part of its periphery to an inside surface of said upper part of said hose portion of said valve body, and said first hose communicating with said balloon for providing a feed of said fluid thereto, said ends of said inner hose being closed by pressing flat and gluing to said inside surface of said hose portion, and a flange connecting portion which passes through said hose portion and said inner hose, and first and second sides of said inner hose being sealingly engaged between projection portions extending from said flange connecting portion and said inside surface of said hose portion.

2. The implantable device as set forth in claim 1, wherein said flattened ends terminate in a wedge configuration so that they blend substantially without a step into said inside surface of said hose portion of said valve body.

3. An implantable device for selectively opening and closing a lumen of a tubular organ of a body, the lumen being bounded by an inner wall of the organ, said implantable device comprising:

an elongate valve body adapted to be introduced into the organ, said valve body including a substantially cylindrically shaped elastic plastic hose portion lining the inner wall of the organ and an inflatable body portion sealingly secured around its periphery to an upper part of said hose portion, support means on said hose portion restricting an increase in diameter of said hose portion, a pump means communicating with said elongate valve body by a first hose, a fluid storage vessel communicating with said pump means by a second hose, and a source of fluid selectively transportable between said storage vessel and said valve body upon actuation of said pump means, said fluid being transportable in a first direction to expand outwardly said inflatable body portion to close a lumen of said hose portion, said fluid being transportable in a second direction to retract said inflatable body to open the lumen.

4. The implantable device as set forth in claim 3, wherein said elastic plastic hose portion is silicone rubber.

5. The implantable device as set forth in claim 3, wherein said support means is constructed of a fabric.

6. The implantable device as set forth in claim 3, wherein said support means is constructed of a fabric inlay.

7. An implantable device for selectively opening and closing a lumen of a tubular organ of a body, the lumen being bounded by an inner wall of the organ, said implantable device comprising:

an elongate valve body adapted to be introduced into the organ, said valve body including a substantially cylindrically shaped hose portion lining the inner wall of the organ and an inflatable body portion sealingly secured around its periphery to an upper part of said hose portion, a pump means communicating with said elongate valve body by a first hose, a liquid storage vessel communicating with said pump means by a second hose, a source of liquid selectively transportable between said storage vessel and said valve body upon actuation of said pump means, said liquid being transportable in a first direction to expand outwardly said inflatable body portion to close a lumen of said hose portion, and said liquid being transportable in a second direction to retract said inflatable body to open the lumen;

said pump means further comprising a manually operable pump member operable to convey said liquid into said inflatable body and said pump means further includes a non-return valve disposed in said second hose from said pump member to said liquid storage vessel and manually actuable from an exterior portion in such a way that, upon actuation of said pump member, said liquid is sucked out of said inflatable body and conveyed into said liquid storage vessel to collapse said inflatable body thereby open the lumen of said hose portion, and upon actuation of said non-return valve said liquid flows under the influence of pressure in said fluid storage vessel into said inflatable body to shut off the lumen of said hose portion.

8. The implantable device as set forth in claim 7, wherein the amount of said liquid in said system comprising said liquid storage vessel, said inflatable body, said pump means and said first and second hoses is such that a given system pressure which is adequate for securely shutting off a through-flow through said valve body is not exceeded.

* * * * *

UNITED STATES PATENT AND TRADEMARK OFFICE
CERTIFICATE OF CORRECTION

PATENT NO. : 5,634,878
DATED : June 3, 1997
INVENTOR(S) : Hans Grundei and Olaf Ahlers, both of Germany It is certified that error appears in the above-identified patent and that said Letters Patent is hereby corrected as shown below:

Column 3, line 62 delete "plop" and insert --pump--.

Signed and Sealed this

Third Day of February, 1998

Attest:

BRUCE LEHMAN

*Attesting Officer*  *Commissioner of Patents and Trademarks*